United States Patent
O'Hara (10) Patent No.: US 6,231,547 B1
(45) Date of Patent: May 15, 2001

(54) EXTERNAL RETAINING DEVICE FOR A CATHETER AND CATHETER ASSEMBLY AND METHOD USING SAME

(75) Inventor: Derek O'Hara, Cloongoona (IE)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/252,259

(22) Filed: Feb. 18, 1999

(51) Int. Cl.$^7$ ........................................ A61M 5/32
(52) U.S. Cl. ................................................ 604/174
(58) Field of Search ........................ 604/174–180; 128/DIG. 26

(56) References Cited

U.S. PATENT DOCUMENTS

| | | |
|---|---|---|
| 3,568,679 | 3/1971 | Reif . |
| 4,193,174 | 3/1980 | Stephens . |
| 4,224,937 | 9/1980 | Gordon . |
| 4,250,880 | 2/1981 | Gordon . |
| 4,261,363 | 4/1981 | Russo . |
| 4,360,025 | 11/1982 | Edwards . |
| 4,397,647 | 8/1983 | Gordon . |
| 4,419,094 | 12/1983 | Patel . |
| 4,435,174 | 3/1984 | Redmond et al. . |
| 4,480,639 | 11/1984 | Peterson et al. . |
| 4,517,971 | 5/1985 | Sorbonne . |
| 4,533,349 | 8/1985 | Bark . |
| 4,632,670 | 12/1986 | Mueller, Jr. . |
| 4,645,492 | 2/1987 | Weeks . |
| 4,659,329 | 4/1987 | Annis . |
| 4,717,385 | 1/1988 | Cameron et al. . |
| 4,932,943 | 6/1990 | Nowak . |
| 4,976,698 | 12/1990 | Stokley . |
| 4,997,421 | 3/1991 | Palsrok et al. . |
| 5,116,324 | 5/1992 | Brierley et al. . |
| 5,242,415 * | 9/1993 | Kantrowitz et al. ............... 604/175 |
| 5,328,487 | 7/1994 | Starchevich . |
| 5,342,324 | 8/1994 | Tucker . |
| 5,370,627 | 12/1994 | Conway . |
| 5,681,290 | 10/1997 | Alexander . |
| 5,690,616 | 11/1997 | Mogg . |
| 5,755,225 | 5/1998 | Hutson . |

FOREIGN PATENT DOCUMENTS

| | | |
|---|---|---|
| 831 757 | 10/1952 | (DE) . |
| 197 49 741 | 5/1998 | (DE) . |
| 0 356 683 | 7/1990 | (EP) . |
| 0 778 041 | 11/1997 | (EP) . |

* cited by examiner

Primary Examiner—Richard K. Seidel
Assistant Examiner—Michael J. Hayes
(74) Attorney, Agent, or Firm—Daniel J. Hulseberg (57) ABSTRACT

An external retaining device, individually or in combination with a catheter having an elongate tube, is provided. The external retaining device includes a base member having a lower surface and an upper surface with a passage extending therethrough. A tube guide portion extending from the upper surface of the base member has two side walls with an elongate channel therebetween. The channel has a first section located proximate the passage and bends upwardly along a smooth transition to a second section angled relative to the first section. A manually-operable clip assembly is located proximate the second section of the channel. The clip assembly preferably includes opposing clip elements mounted for pivotal movement between an open position and a closed position. Preferably, pivotal movement is accomplished by forming the side walls of elastic material and affixing each clip element to a corresponding side wall, such that flexure of the side walls toward each other moves the clip elements to the open position. The elongate tube of the catheter is thereby directed through the passage and positioned within the channel to form a smooth 90° bend, and secured in place at the second section of the channel with the clip assembly moved to the closed position. An internal retaining device also can be used in combination with the external retaining device.

21 Claims, 7 Drawing Sheets

EXTERNAL RETAINING DEVICE FOR A CATHETER AND CATHETER ASSEMBLY AND METHOD USING SAME

BACKGROUND OF THE INVENTION

1. Field of the Invention

The present invention relates to a device for retaining a catheter, such as a gastrostomy or jejunostomy feeding tube, in place with respect to the skin of a patient. The present invention also relates to a catheter assembly and a method of using the same.

2. Description of Related Art

It is common practice in health care facilities or the like for an elongate flexible tube, generally known as a catheter, to be inserted percutaneously in a patient to assist in medical treatment. Such catheters are used in a variety of applications to inject fluids into or withdraw fluids from the canals, vessels, passageways or body cavities of a patient. Catheters also can be used to maintain an orifice or similar passage in an open condition.

For example, numerous patients receiving medical treatment are unable to ingest foods orally due to conditions such as facial injuries, esophageal injuries, or unconsciousness. Liquid nutritional products therefore have been developed for a process known as enteral feeding. Enteral feeding typically involves the insertion of a feeding tube percutaneously into the gastrointestinal tract of a patient, such as the stomach or intestine. To prevent injury to the patient and the feeding assembly, it is advantageous to retain the placement of the feeding tube relative to the skin of the patient. A variety of retaining devices have been developed for this purpose.

Figure 1:
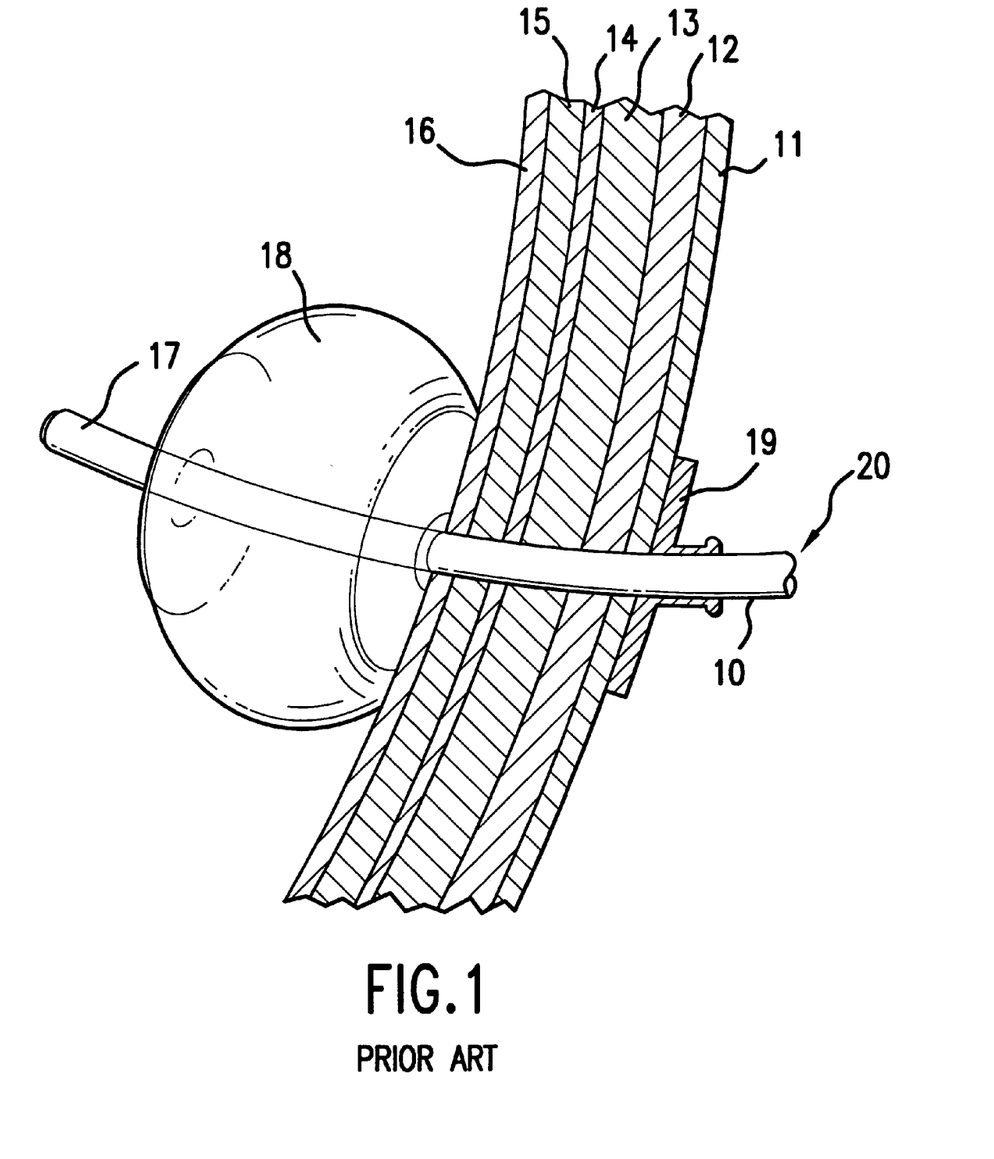
FIG. 1 is a schematic representation of a gastrostomy tube using a known external retaining device.

FIG. 1 demonstrates, for purpose of illustration only, a known catheter or feeding tube assembly including a gastrostomy tube 10 inserted percutaneously in a patient for the introduction of a liquid nutritional product. The gastrostomy tube 10 extends through the epidermis 11, the fat layer 12, the muscle layer 13, the peritoneum 14, the stomach lining 15, and the gastric mucosa 16. One end 17 of the gastrostomy tube is located within the stomach. An internal retaining member 18 is fastened proximate one end of the gastrostomy tube and located within the stomach, adjacent to the mucosa wall 16. The internal retaining member 18 thereby reduces the possibility of inadvertent removal of the gastrostomy tube from the patient. As shown in FIG. 1, the internal retaining member can be an inflatable or expandable membrane, although it also is known to use a flange-type internal retaining member if desired. Furthermore, it is noted that catheter assemblies used for other applications, such as for jejunostomy or intravenous applications, may not require an internal retaining device.

The known feeding tube assembly of FIG. 1 further includes an external retaining device 19 located externally of the person adjacent to the epidermis 11. This particular external retaining device generally is a disk-shaped member having a cylindrical opening formed therethrough to maintain the feeding tube substantially perpendicular to the patient's skin. Similar external retaining devices are available for use with enteral feeding tubes distributed by Sandoz Nutrition Corporation, 5320 West Twenty Third Street, P.O. Box 370, Minneapolis, Minn. 55440, U.S.A., under trade names such as CALUSO® PEG and SUPER PEG™. Although the Sandoz external retaining device has a circular base portion, other shapes can be used, as demonstrated by U.S. Pat. No. 5,071,405. Because the feeding tube extends perpendicularly from the patient, this known feeding tube assembly can be susceptible to entanglement. To minimize such entanglement, it is advisable that the tube of this feeding tube assembly be wrapped or twisted into a loop. Care must be taken, however, to ensure that subsequent pulling or tugging does not kink the loop and thus occlude flow through the tube.

Several concepts for external retaining devices, which are also known in the medical device industry as skin disks, have been developed in an attempt to minimize or eliminate the disadvantages of the prior art design. Particularly, U.S. Pat. No. 5,267,969 discloses an external retaining device configured to receive a feeding tube extending substantially perpendicularly from a patient and then guide the feeding tube through a 90° bend without being kinked. The external retaining device of U.S. Pat. No. 5,267,969 includes a first hole to receive the feeding tube and a second hole of a larger diameter having a center axis arranged coplanar with but perpendicular to the center axis of the first hole. Although effective for its intended purpose, it has been found that this external retaining device can be difficult to adjust in position once properly placed against the patient with the feeding tube extending therethrough.

In view of the above, there remains a need for a readily adjustable external retaining device capable of bending and retaining a catheter in position against a patient without being kinked or occluded. Furthermore, there remains a need for a feeding tube assembly including this improved external retaining device and a method of using the same.

SUMMARY OF THE INVENTION

The purpose and advantages of the present invention will be set forth in and apparent from the description that follows, as well as will be learned by practice of the invention. Additional advantages of the invention will be realized and attained by the apparatus and method particularly pointed out in the written description and claims hereof, as well as from the appended drawings.

To achieve these and other advantages and in accordance with the purpose of the invention, as embodied and broadly described, the invention includes an external retaining device for use with a catheter having an elongate tube. The present invention also includes the catheter assembly incorporating the external retaining device and the method of using the same.

The external retaining device includes a base member having a lower surface and an upper surface. A passage having a central axis is defined between the lower and upper surfaces of the base member. Preferably, a tube guide portion extends from the upper surface of the base member. The tube guide portion has an elongate channel with a longitudinal axis defined therein. A first section of the channel is located proximate the passage with the longitudinal axis at the first section of the channel aligned substantially with the central axis of the passage. The second section of the channel is spaced from the first section of the channel with the longitudinal axis at the second section of the channel angled relative to the central axis of the passage. In this manner, the elongate tube can be directed through the passage and positioned within the channel to form approximately a 90° bend in the tube along a smooth transition without kinking or pinching of the tube.

A manually-operable clip assembly is provided on the base member to secure the placement of the external retaining device relative to the elongate tube and, thus, placement of the elongate tube relative to the base portion of the external retaining device. The clip assembly is moveable selectively between a closed position and an open position. The elongate tube thereby can be received by the clip assembly when the clip assembly is in the open position and secured in place, without occlusion, when the clip assembly is in the closed position.

In the preferred embodiment of the present invention, the clip assembly is located on the tube guide portion proximate the second section of the channel. Furthermore, the clip assembly preferably includes opposing clip elements mounted to the tube guide portion proximate the second section of the channel. Pivotal movement is accomplished by forming the side walls of the tube guide portion with an elastic material and affixing each clip element to a corresponding side wall such that flexure of each side wall toward the other moves the clip element to the open position. A finger grip can be provided on each side wall to further enhance flexure. The base member and the tube guide portion are preferably formed together as a single-piece polyurethane member, with the clip elements made of relatively rigid plastic and embedded in the corresponding side walls.

It is to be understood that both the foregoing general description and the following detailed description are exemplary and are intended to provide further explanation of the invention claimed.

BRIEF DESCRIPTION OF THE DRAWINGS

The accompanying drawings, which are incorporated in and constitute part of this specification, are included to illustrate and provide a further understanding of the apparatus and method of the invention. Together with the description, the drawings serve to explain the principles of the invention.

DETAILED DESCRIPTION OF THE INVENTION

Reference will now be made in detail to the preferred embodiments of the present invention, an example of which is illustrated in the accompanying drawings. The method and corresponding steps of the invention will be described in conjunction with the detailed description of the device and assembly.

The external retaining device of the present invention, as properly modified for size and its intended application, can be used in combination with any of a variety of catheters. The external retaining device of this invention is particularly suited for use with either a gastrostomy or a jejunostomy feeding tube assembly having an elongate tube to be placed percutaneously in a patient. For purpose of illustration, and not limitation, reference therefore will be made to the construction and use of an external retaining device for a feeding tube assembly. It is recognized, however, that modifications can be made for alternative catheter applications. As such, the term "elongate tube" or "tube" as used herein is intended to represent all reasonable catheter applications, unless otherwise noted.

Figure 2:
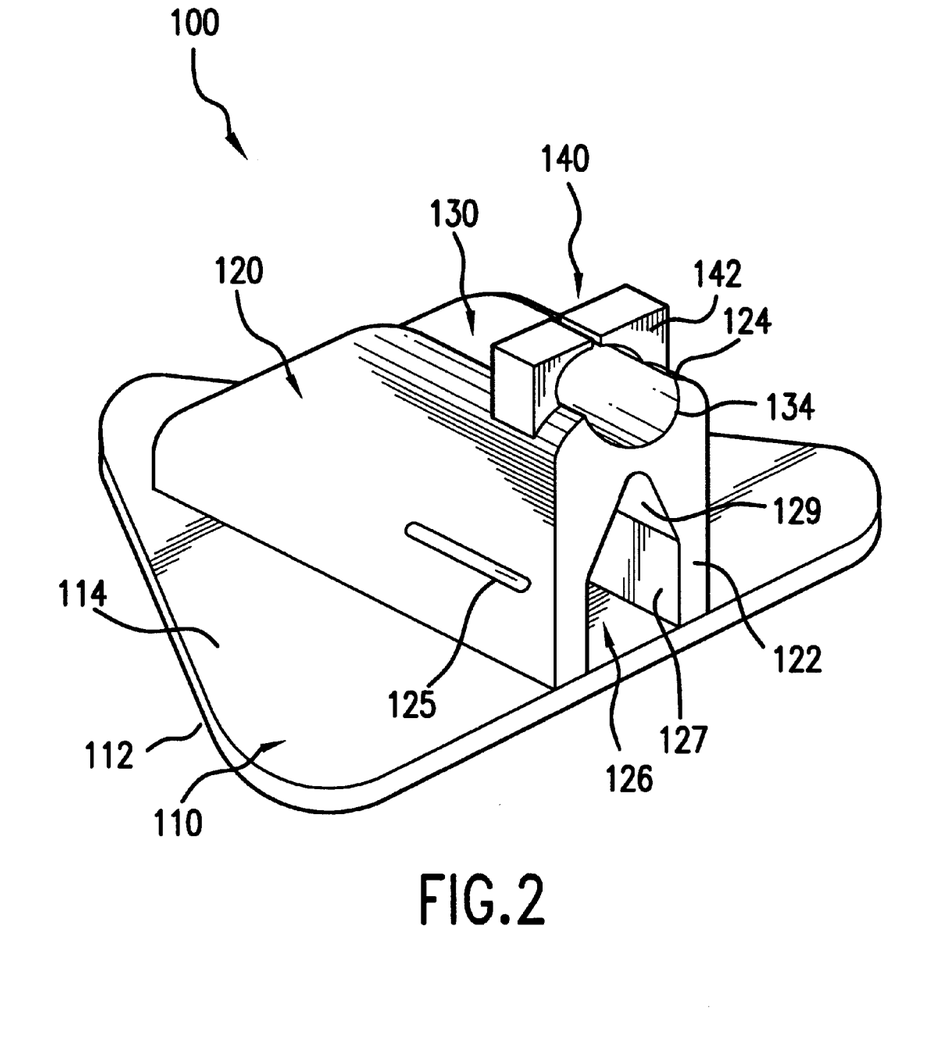
FIG. 2 is a perspective view of a representative embodiment of the external retaining device of the present invention.

An exemplary embodiment of the external retaining device of the present invention is shown in FIGS. 2–5 and designated generally by reference character 100. In accordance with the present invention, and as embodied herein, the external retaining device 100 includes a base member 110 having a lower surface 112 and an upper surface 114. As used herein and in the claims, such terms as "upper", "upwardly" and "lower" are intended to define a spatial relationship relative to the lower surface 112 of the base member 110 when resting upon a horizontal surface as depicted in FIG. 2.

Figure 3:
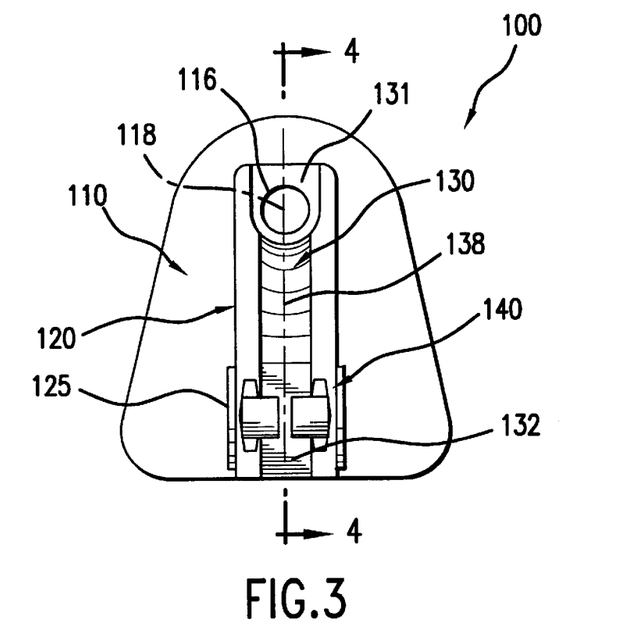
FIG. 3 is a top view of the external retaining device of FIG. 2.
Figure 4:
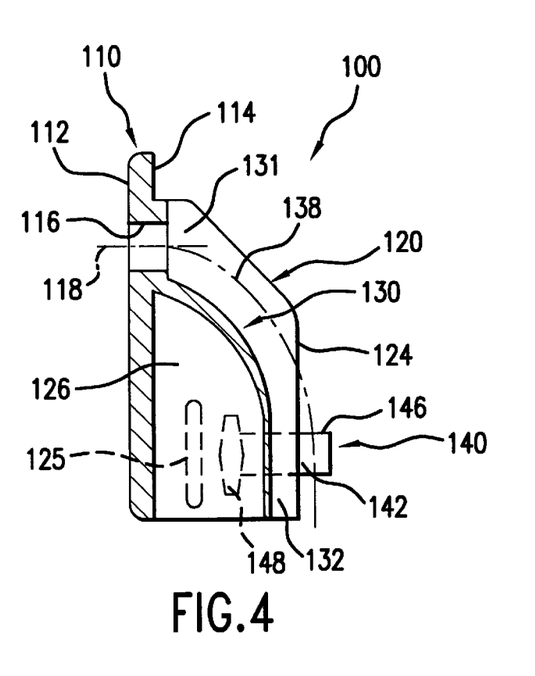
FIG. 4 is a cross-sectional side view of the external retaining device of FIG. 2, taken along line 4—4 in FIG. 3.
Figure 5:
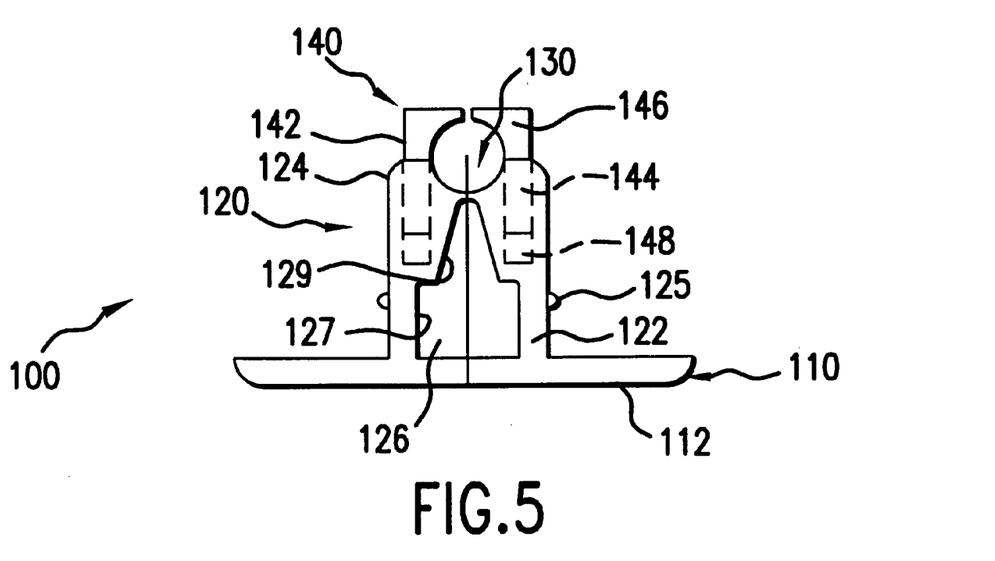
FIG. 5 is a back view of the external retaining device of FIG. 2.

The lower surface 112, as shown in FIGS. 4 and 5, is configured so as to be placed flush against or rest flush upon the skin of the patient. Although shown as a planar surface, the lower surface 112 can be contoured so as to be convex or concave, or both, if desired for a particular application, or can be corrugated to allow the access of air to the underlying skin. Similarly, FIGS. 2 and 5 show the upper surface 114 as having a planar configuration, although alternative surface configurations can be provided if desired. In the preferred embodiment, and as shown in FIGS. 4 and 5, the upper and lower surfaces are both planar and parallel with each other. FIG. 3 shows the base member 110 of the preferred embodiment as having a generally triangular shape with rounded corners, although alternative shapes likewise can be used such as circular, rectangular or irregular geometric shapes.

The base member 110 of the external retaining device 100 embodied herein also has a passage 116 with a central axis 118 defined therein. The passage 116 extends between the lower surface 112 and the upper surface 114 of the base member 110, and is sized and shaped to receive a tube of a known cross-section therethrough. Preferably, the passage is sized and shaped so as to create a friction or interference fit with the elongate tube, although still allow sliding or longitudinal movement of the elongate tube through the passage when an appropriate force is applied as desired. For example, and not by limitation, the passage 116 preferably would be a circular aperture having a diameter of 0.206 inches for use in combination with an elongate tube made of polyurethane having an outer diameter of 0.209 inches (16 French). In this manner, an elongate tube extending percutaneously from a patient can be directed through the passage 116 and frictionally held therein.

FIGS. 3 and 4 show the passage 116 as a circular aperture extending through the base member 110, such that the tube would be inserted axially along the central axis 118 of the passage 116. Alternatively, the passage can be defined as an open recess, such as a horseshoe or omega shaped recess, formed along a peripheral edge of the base member 110. In this manner, and with the base member 110 formed of a soft elastic material, the elongate tube can be inserted transversely into the passage from the peripheral edge of the base member 110 rather than being directed axially therein. As previously describe, however, the passage preferably would be sized to create a friction fit with the elongate tube directed therein.

As embodied herein, the base member 110 of the external retaining device 100 is provided with a tube guide portion. FIGS. 2–5 shows the tube guide portion 120 extending from the upper surface 114 of the base member 110, and having an elongate channel 130 with a longitudinal axis 138 defined therein. A first section of the channel 130 is located proximate the passage 116 with the longitudinal axis 138 at the first section 131 of the channel 130 aligned substantially with the central axis 118 of the passage 116. As such, an elongated tube extending from the patient and directed through the passage 116 can be positioned readily in the channel 130 of the tube guide portion 120.

The elongate channel 130 of the preferred embodiment has an opposite second section 132 spaced from the first section 131 of the channel 130. As shown best in FIG. 4, the longitudinal axis 138 at the second section 132 of the channel 130 is preferably angled relative to the central axis 118 of the passage 116. Particularly, and as embodied herein, the longitudinal axis 138 at the second section 132 of the channel 130 is coplanar with and angled about 900 relative to both the central axis 118 of the passage 116 and the longitudinal axis 138 at the first section 131 of the channel 130. FIG. 4 further shows that the channel 130 is configured to provide a substantially smooth transition from the first section 131 of the channel 130 to the second section 132 for an elongate tube positioned therein. This smooth transition minimizes risk of kinking or pinching of the elongate tube within the channel 130. To further retain the elongate tube, and as best shown in FIGS. 2 and 5, the channel 130 of the preferred embodiment also has a concave surface 134 along its length that is complimentary to the outside surface of the elongate tube and of sufficient depth to inhibit lateral movement of the tube once positioned within the channel 130.

To support the desired channel configuration, the tube guide portion 120 embodied herein includes two side walls 122 extending upwardly from the base member 110. FIGS. 3 and 5 show the two walls as being substantially planar and parallel with each other, although alternative shapes can be used. The side profile formed by the upper edge area 124 of each side wall 122 can have an angular ramp configuration, as shown in FIG. 4. Alternatively, the upper edge area 124 can generally follow the contour of the channel 130 along its length from the first section 131 to the second section 132, or can be provided with any other acceptable geometric configuration. As embodied herein, the channel 130 is located between the side walls 122 proximate an upper edge area 124 of each side wall 122 for easier positioning of the elongate tube therein. Below the channel 130 and between the side walls 122, the tube guide portion 120 can be made of a solid construction or, as shown in FIGS. 4 and 5 and described in detail below, the two side walls 122 can define a hollow space 125 therebetween.

Further in accordance with the invention, a manually-operable clip assembly is provided on the base member 110 to secure placement of the external retaining device along the elongate tube directed through the passage. The clip assembly is moveable selectively between a closed position and an open position. Particularly, the clip assembly is configured and located on the base member 110 such that an elongate tube directed through the passage 116 can be received by the clip assembly when the clip assembly is in the open position and secured in place without occlusion thereof when the clip assembly is in the closed position. Because the clip assembly is readily moveable between the closed and open position, the placement of the external retaining device 100 relative to the elongate tube and, thus, placement of the elongate tube relative to the base member 110 of the external retaining device 100 can be adjusted and secured more readily.

A variety of clip assembly configurations can be used in accordance with the present invention. As embodied herein, the manually-operable clip assembly 140 includes at least one clip element 142 mounted to the base member 110 for pivotal movement between the open position and the closed position. Although only one clip element 142 need be provided, if appropriately sized to secure placement of the elongate tube relative to the base portion, it is preferable to provide two or more such clip elements 142.

The clip assembly 140 of the external retaining device 100 embodied herein includes opposing clip elements 142 mounted to the base member 110. The opposing clip elements 142 are sufficiently spaced apart to allow the elongate tube to be received therebetween when the clip assembly 140 is in the open position, and captured or secured in place by the clip elements 142 without occlusion of the tube when the clip assembly 140 is in the closed position. Preferably, the clip elements 142 are coplanar with each other as shown in FIGS. 2, 3 and 5, although they can be offset from each other if desired. At least one of these clip elements 142 is mounted for pivotal movement between the open position and the closed position in accordance with the invention. It is preferred, however, that both clip elements 142 are capable of such pivotal movement for enhanced operation of the clip assembly 140.

The clip element 142 embodied herein includes a stem 144 having a hook shaped distal end 146. In this manner, the clip element 142 can be mounted at its stem 144 such that the hook shaped distal end 146 can be moved into and out of position to capture or entrap the elongate tube without occlusion thereof. For example, and as embodied herein, FIGS. 2–6 show opposing clip elements 142 mounted along the second section of the channel 130 defined in the tube guide portion 120, with at least one clip element 142 mounted on each side of the channel 130. Each clip element 142 is mounted with the stem 144 located proximate the upper edge area 124 of the corresponding side wall 122 and the hook shaped distal end 146 extending transversely across at least a portion of the channel 130 when the clip element 142 is in the closed position. If more than one clip element 142 is used, as shown, then the clip elements 142 preferably are substantially identical. Although it is possible to form the clip elements 142 integrally with the corresponding side wall 122 as a single piece, each clip element 142 is preferably made as a separate piece using a relatively rigid plastic material such as polycarbonate or the like. Alternative materials that can be used include cyrolite acrylic or an acrylonitrile-butadiene-styrene ("ABS")resin.

Pivotal movement of the clip element can be accomplished using a spring hinge connection to bias the clip element toward the closed position. Such a pivotal configuration would preferably include a finger engaging tab extending from the clip element to allow the clip element to be engaged and moved manually by the operator to the open position. Upon release of the tab, the clip element would return to the closed position due to the bias of the spring hinge. The spring hinge connection can be provided as a separate element interconnecting the clip element to the base member, or can be formed integrally as a living hinge if the clip element and the base member are made together as a single piece.

Alternatively, pivotal movement of the clip element 142 can be accomplished by flexure of the tube guide portion 120 itself. For example, and with the clip assembly 140 located on the tube guide portion 120 of the base member 110 as embodied herein, at least one side wall 122 of the tube guide portion 120 is made elastic for flexure toward the other side wall 122. With at least one clip element 142 mounted proximate the second section 132 of the channel 130 at the upper edge area 124 of the elastic side wall 122, the clip element 142 can be moved pivotally from the closed position to the open position by flexure of the elastic side wall 122 as shown by arrow A in FIG. 6. The clip element 142 can be affixed to an exposed surface of the side wall 122 or, in accordance with the preferred embodiment of the present invention, can be embedded directly into the elastic side wall 122 using known construction or molding techniques. Preferably, the clip element 142 includes a pad formed at the proximal end 148 of the stem 144, which is embedded in the upper edge area 124 of the side wall 122.

Figure 6:
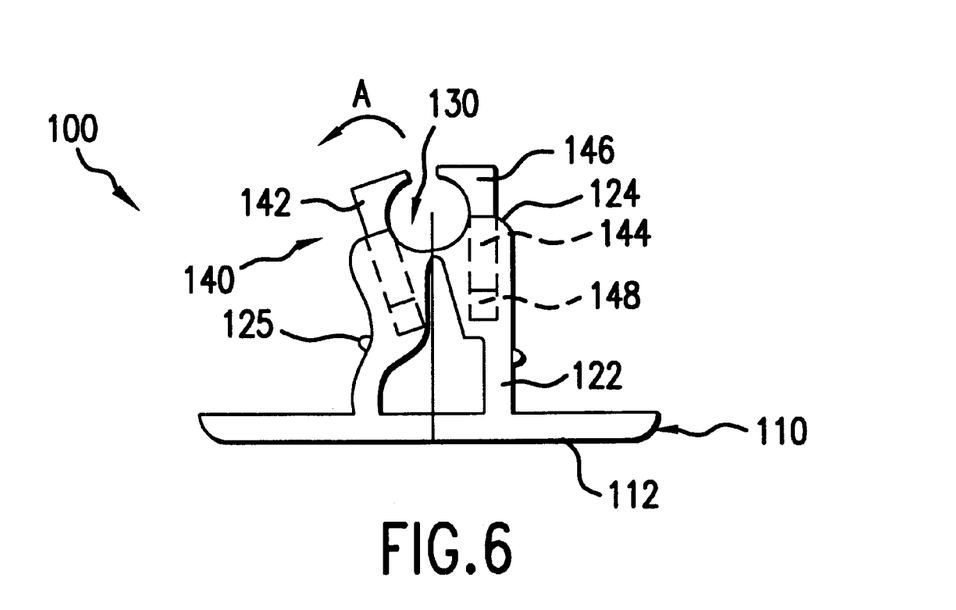
FIG. 6 is a schematic back view of the external retaining device of FIG. 2, showing the flexure of a side wall to move a corresponding clip element to an open position.

In the preferred embodiment of the present invention, both side walls 122 are elastic for flexure toward each other. Each side wall 122 has at least one clip element 142 of the clip assembly 140 mounted to be moved pivotally from the closed position to the open position by flexure of the corresponding side wall 122. FIG. 6 shows the flexure of only one side wall for purpose of comparison with the opposite side wall in the unflexed state. To further facilitate pivotal movement of the clip elements 142, each side wall 122 is provided with a finger grip 125, such as a rib or detent, which identifies the location best to apply pressure for flexure of the corresponding side wall 122. Pressure is generally applied to the side walls 122, although not necessarily, using the thumb and index finger of the operator. Upon release of the applied pressure, the elastic side walls 122 return automatically to the original unflexed condition, as shown in FIG. 5, so as to move the clip elements 142 to the closed position due to the memory of the elastic material used.

As previously noted, and as shown in FIGS. 4–6, the two side walls 122 preferably define a hollow space 125 therebetween. Particularly, FIG. 5 shows a hollow space 125 having a generally rectangular lower cross-sectional section defined by the inner surface 127 of the planar side walls 122, and a generally triangular upper cross-sectional section defined by tapered surfaces 129 formed beneath the channel 130 in the upper edge area 124 portion of the side walls 122. In this manner, a "living hinge" is defined at the apex of the tapered surfaces 129 to further facilitate flexure of the side walls 122 and, thus, movement of the clip elements 142 from the closed position to the open position.

The tube guide portion 120 can be constructed separate from the base member 110, either of the same material or of different material, and then joined together. In the preferred embodiment, however, the base member 110 and the tube guide portion 120 are formed together as a single piece. A soft, yet durable, elastic material such as polyurethane, silicone rubber, or any other suitable elastomeric material can be used, although polyurethane is preferred. Alternatively, it is possible to form the tube guide portion 120, either individually or together with the base member 110, as a solid structure with no hollow space using a conventional foam material encased in a skin or film of vinyl, plastic or a similarly durable material. Known construction or molding techniques, such as insertion molding, injection molding or rotational molding, can be used.

The preferred dimensions of the base member, including the tube guide portion if provided, will depend upon the size and type of elongate tube used for the catheter assembly, as well as its intended application. For purpose of example, but not by limitation, the generally triangular shaped base member, as shown in FIGS. 2–5, if sized for use with a 16 French gastrostomy feeding tube would preferably, but not necessarily, have an overall length of about 1.5 inches, an overall width of about 1.3 inches, and an overall height of about 0.7 inches.

If desired, the base member 110 can be provided with one or more holes (not shown) defined therein to attach the external retaining device 100 to the patient. These holes thus allow the use of sutures, staples or similar fasteners to attach the external retaining device 100 to the patient's skin. Alternatively, the external retaining device 100 can be attached using known adhesives or bandages if desired. In the preferred embodiment, however, an internal retaining device is provided at the internally-located end of the elongate tube, as shown for purpose of example in FIGS. 7 and 8, which would effectively assist in maintaining the placement of the external retaining device.

In operation, and referring to the external retaining device 100 previously described in detail as well as to FIGS. 2–7 for purpose of example, the method of retaining a catheter assembly to a patient in accordance with the present invention involves directing the elongate tube 70 of the catheter assembly through the passage 116 of the base member 110 of the external retaining device 100, and positioning the elongate tube within the channel 130 of the tube guide portion 120. These steps can be performed either before the elongate tube has been placed percutaneously in the patient or, as in the preferred embodiment of the invention, performed after such percutaneous placement.

The method of the present invention further includes moving the clip assembly 140 to the open position, and inserting the elongate tube 70 into the clip assembly 140. In accordance with the preferred embodiment above, this is performed by applying pressure to each elastic side wall 122 of the tube guide portion 120 to move the clip element 142 pivotally from the closed position to the open position by flexure of the elastic side wall 122. Particularly, when both side walls 122 are elastic, this step involves squeezing the side walls 122 toward each other to move each clip element 142 pivotally from the closed position to the open position by flexure of the corresponding side wall 122. Once properly placed, such as with the lower surface 112 of the base member 110 at a desired location along the length of the elongate tube, the clip assembly 140 is closed to secure the elongate tube at the second section 132 of the channel 130. With the preferred embodiment of the invention, this is accomplished simply by releasing the elastic side walls 122 to return the clip elements 142 to the closed position.

As previously noted, an internal retaining device 100 can be used in combination with the external retaining device 100 of the present invention. This is particularly likely when the catheter assembly is a gastrostomy feeding tube assembly. Among other things, the interaction of the internal retaining device 100 and the external retaining device 100 generally assists in retaining proper placement of the elongate tube. Additionally, the external retaining device 100 can be attached to the patient by secondary means, if desired, such that the placement of the catheter assembly is further retained. This can be accomplished using a known adhesive or, if holes are provided in the base member 110 of the external retaining device 100, using sutures, staples or similar known fasteners.

It is noted that an advantage of the present invention is the ease in which the external retaining device 100 can be adjusted or moved along the length of the elongate tube. For example, if treatment or cleaning of the stoma or skin beneath the external retaining device 100 is required, the clip elements 142 can be moved readily to the open position to allow the external retaining device 100 to be slid or otherwise moved to an alternate or adjusted position. Once treatment is completed, the external retaining device 100 is repositioned and secured in place as previously described.

Figure 7:
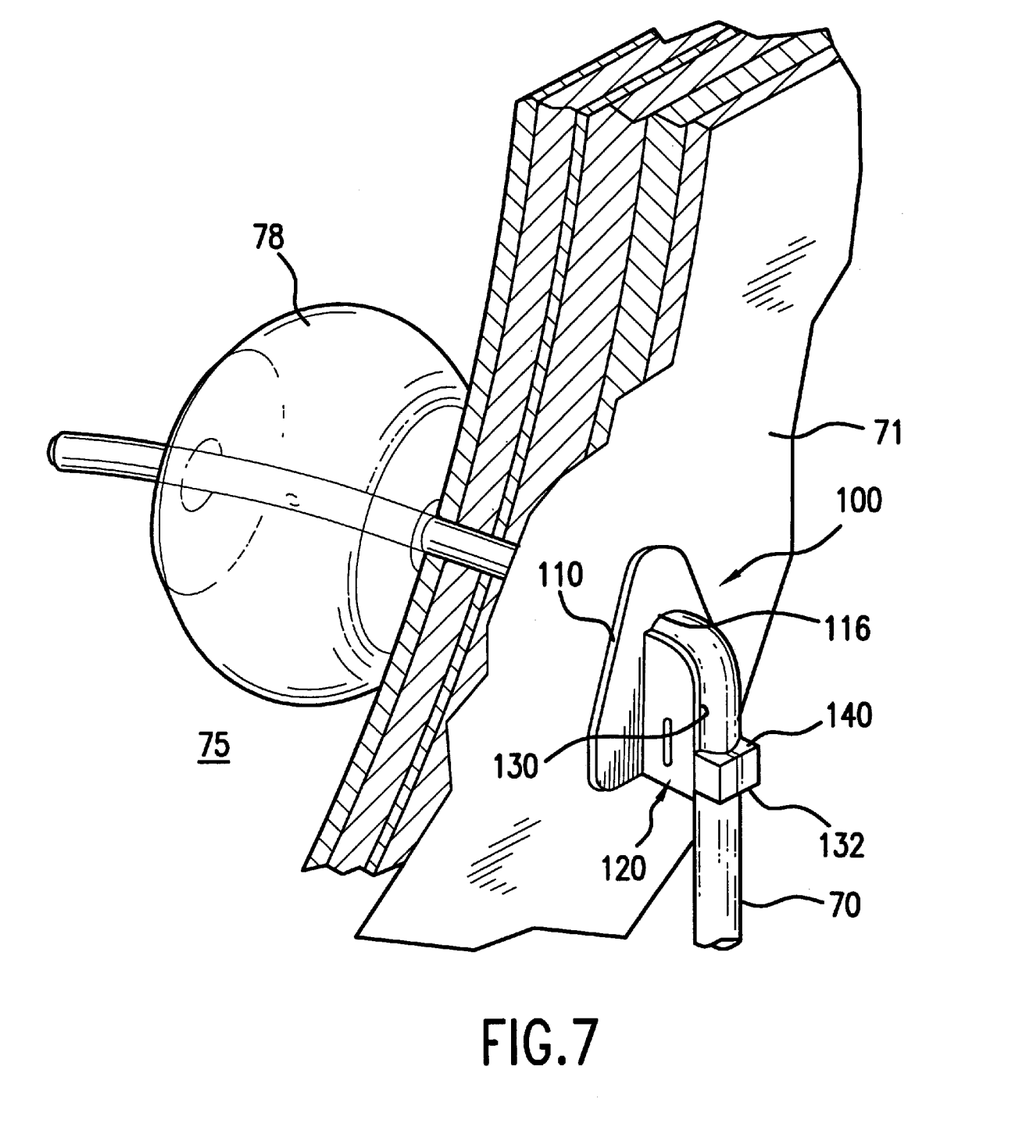
FIG. 7 is a schematic representation of a catheter assembly including a gastrostomy tube and an external retaining device in accordance with the present invention.

Application of the apparatus and method of the present invention can be better understood by reference to FIG. 7, in conjunction with FIGS. 2–5. That is, FIG. 7 shows one embodiment of a catheter assembly as properly retained in accordance with the present invention. A gastrostomy tube 70 extends percutaneously via a stoma through several layers of body tissue as previously described with regard to FIG. 1 and into the stomach 75 of a patient. An internal retaining member 78, which in this embodiment is an expandable membrane as is well known in the art, is disposed adjacent to the mucosa of the stomach 75. The lower surface 112 of the external retaining device 100 is positioned flush against the patients's skin 71. The passage 116 defined in the base member 110 extends substantially perpendicular to the patient's skin 71 and is aligned proximate the stoma, such that the gastrostomy tube 70 can be directed therethrough. The external or exposed portion of the gastrostomy tube 70 is then positioned within the channel 130 so as to bend 90° along a smooth transition into an alignment substantially parallel with the patient's skin 71. The gastrostomy tube 70 proximate the second section of the channel 130 is releasably secured in the clip assembly 140 with the clip elements 142 in the closed position as previously described.

Figure 8:
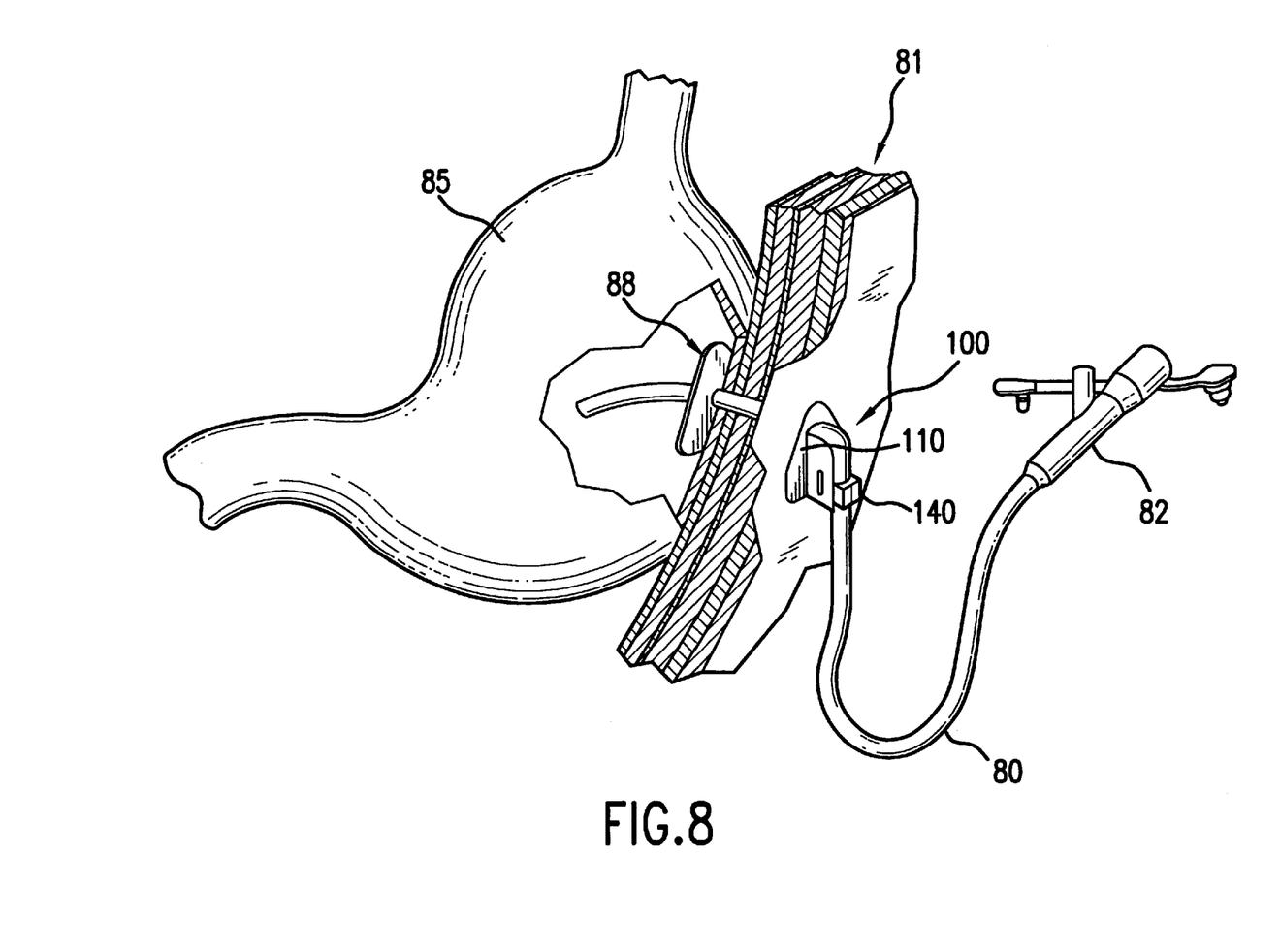
FIG. 8 is a schematic representation of another catheter tube assembly including a gastrostomy tube and an external retaining device in accordance with the present invention.

Referring next to FIG. 8 there is shown an alternative gastrostomy tube 80 passing percutaneously via a stoma through several layers of body tissue, as previously described with regard to FIG. 1, and into the stomach 85 of a patient. The external retaining device 100 of the present invention is applied in the same manner as described with regard to the embodiment of FIG. 7. Unlike the catheter assembly of FIG. 7, however, this embodiment has a flange-type internal retaining member 88 similar to that of U.S. Pat. No. 5,080,650, which is incorporated by reference herein. Furthermore, the gastrostomy tube assembly of FIG. 8 preferably includes a connector 82 to allow the feeding tube 80 to be connected to a fluid source, such as for the introduction of a liquid nutritional product or supplement. Examples of such connectors include a Y-port as disclosed in U.S. Design Pat. No. 308,576 and U.S. Pat. No. 5,057,093, which are incorporated herein by reference.

Figure 9:
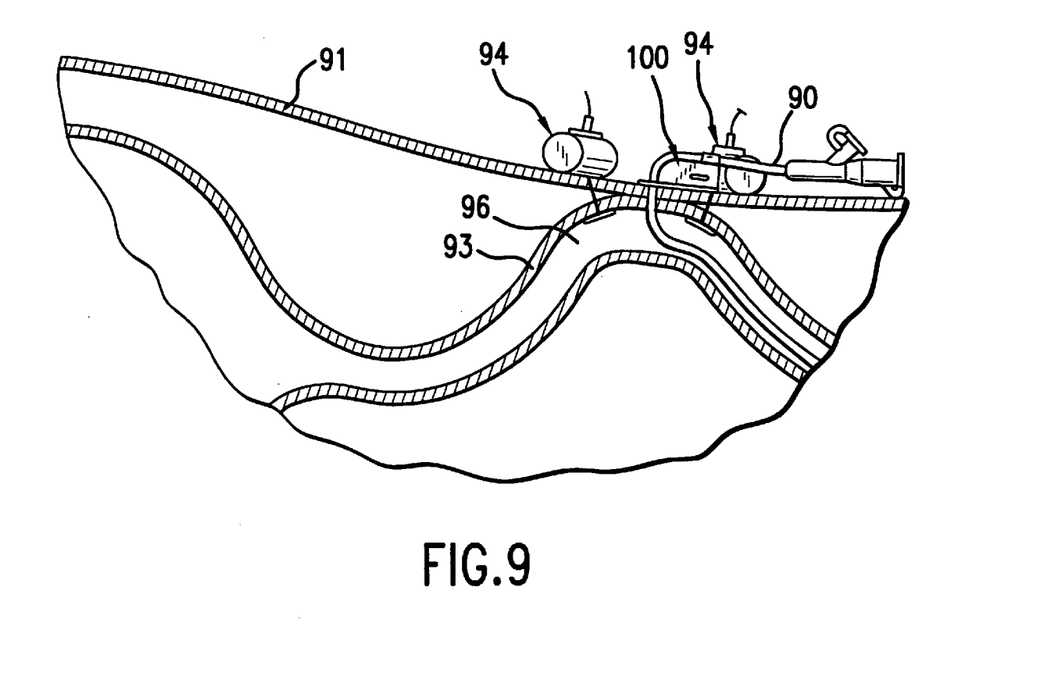
FIG. 9 is a schematic representation of an additional catheter assembly including a jejunostomy tube and an external retaining device in accordance with the present invention.

Yet another application of the apparatus and method of the present invention is shown in FIG. 9. Particularly, FIG. 9 is directed to a jejunostomy tube assembly including the external retaining device 100. The jejunostomy tube 90 passes through the abdominal wall 91 and the intestinal wall 93 to be located in the jejunum 96 of the patient. During placement of the tube assembly, the intestine 93 is secured adjacent the abdominal wall using fastener assemblies 94, of the type taught in U.S. Patent RE 34,021 and incorporated herein by reference. Preferably, such fasteners need be used only temporarily until a stoma has been adequately formed. A jejunostomy tube typically has a diameter much smaller than a gastrostomy tube and, therefore, the dimensions of the external retaining device 100 must be modified accordingly. Additionally, it is noted from FIG. 9 that no internal retaining device is fastened to the jejunostomy tube 90 itself.

Although the peristaltic action of the intestines can exert forces on the jejunostomy tube 90 capable of causing a portion of the tube to back-out of the body via the stoma, the interference fit created between the jejunostomy tube 90 and the external retaining device 100 will minimize such movement. That is, if appropriately dimensioned, an interference fit will be created between the jejunostomy tube 90 and the passage 116, and further enhanced by the resistance resulting from the bend configuration of the channel 130 and the forces exerted by the clip assembly 140.

It will be apparent to those skilled in the art that various modifications and variations can be made in the apparatus and method of the present invention without departing from the spirit or scope of the invention. Thus, it is intended that the present invention include modifications and variations that are within the scope of the appended claims and their equivalents.

What is claimed is:

1. An external retaining device for use with a catheter, the retaining device comprising:

a base member having a lower surface and an upper surface, the base member defining a passage therethrough from the lower surface to the upper surface, the passage having a central axis and configured for an elongate tube of a catheter to be directed therethrough, the base member including a tube guide portion extending from the upper surface, the tube guide portion having two side walls extending upwardly from the base member and an elongate channel with a longitudinal axis defined therein, the channel being located between the side walls proximate an upper edge area of each side wall, at least one side wall being elastic for flexure toward the other side wall; and a manually-operable clip assembly located proximate the channel of the tube guide portion, the clip assembly including at least one clip element mounted for pivotal movement selectively between a closed position and an open position, the at least one clip element of the clip assembly being mounted proximate the upper edge area of the elastic side wall for pivotal movement from the closed position to the open position by flexure of the elastic side wall toward the other side wall, the clip assembly capable of receiving an elongate tube directed through the passage when the clip assembly is in the open position and securing placement of the elongate tube relative to the base member when the clip assembly is in the closed position.

2. An external retaining device according to claim 1 wherein the channel has a first section located proximate the passage, the longitudinal axis at the first section of the channel aligned substantially with the central axis of the passage, the channel having a second section spaced from the first section of the channel with the longitudinal axis at the second section of the channel angled relative to the central axis of the passage; and further wherein the clip assembly is located proximate the second section of the channel for securing the elongate tube within the channel when the clip assembly is in the closed position.

3. An external retaining device according to claim 1 wherein the clip assembly includes opposing clip elements mounted proximate the channel of the tube guide portion, one clip element mounted on each side of the channel and coplanar with the other clip element, at least one of the clip elements being mounted for pivotal movement between the open position and the closed position.

4. An external retaining device according to claim 1 wherein the clip element of the clip assembly is mounted proximate the upper edge area of the elastic side wall, the clip element being moved pivotally from the closed position to the open position by flexure of the elastic side the at least one clip element has a hook-shaped distal end extending transversely across at least a portion of the channel when in the closed position.

5. An external retaining device according to claim 4 wherein the at least one clip element includes a stem affixed to the upper edge area of the elastic side wall.

6. An external retaining device according to claim 5 wherein the clip element further includes a pad formed at a proximal end of the stem and embedded in the upper edge area of the elastic side wall.

7. An external retaining device according to claim 5 wherein the clip element is made of a rigid material.

8. An external retaining device according to claim 4 wherein the two side walls are elastic for flexure toward each other, at least one clip element of the clip assembly being mounted at the upper edge area of each side wall to be moved pivotally from the closed position to the open position by flexure of the side wall toward the other side wall.

9. An external retaining device according to claim 8 wherein each side wall has a finger grip for flexure of the side wall.

10. An external retaining device according to claim 8 wherein the two side walls of the tube guide portion define a hollow space therebetween.

11. An external retaining device according to claim 8 wherein the tube guide portion and the base member are formed of polyurethane.

12. An external retaining device according to claim 8 wherein the tube guide portion and the base member are formed together as a single piece.

13. An external retaining device according to claim 2 wherein the longitudinal axis at the second section of the channel is coplanar with and angled about 90° relative to the central axis of the passage and the longitudinal axis at the first section of the channel.

14. An external retaining device for use with a catheter, the retaining device comprising:
a base member having a lower surface and an upper surface, the base member defining a passage therethrough from the lower surface to the upper surface, the passage having a central axis and configured for an elongate tube of a catheter to be directed therethrough, the base member including a tube guide portion extending from the upper surface, the tube guide portion having two side walls extending upwardly from the base member, at least one side wall being elastic for flexure toward the other side wall, the tube guide portion further having an elongate channel with a longitudinal axis defined therein, the channel being located between the side walls proximate an upper edge thereof, the channel having a first section located proximate the passage, the longitudinal axis at the first section of the channel aligned substantially with the central axis of the passage, the channel having a second section spaced from the first section of the channel with the longitudinal axis at the second section of the channel angled relative to the central axis of the passage; and
a manually-operable clip assembly located on the tube guide portion of the base member proximate the second section of the channel, the clip assembly being moveable selectively between a closed position and an open position, the clip assembly including at least one clip element mounted proximate the channel at the upper edge area of the elastic side wall, the clip element being moved pivotally from the closed position to the open position by flexure of the elastic side wall toward the other side wall, the clip assembly capable of receiving an elongate tube directed through the passage when the clip assembly is in the open position and securing placement of the elongate tube relative to the base member when the clip assembly is in the closed position.

15. An external retaining device according to claim 14 wherein the two side walls are elastic for flexure toward each other, at least one clip element of the clip assembly being mounted at the upper edge area of each side wall to be moved pivotally from the closed position to the open position by flexure of the side wall toward the other side wall, and further wherein the clip element includes a stem having a hook shaped distal end, the clip element being mounted with the stem affixed to the upper edge area of the side wall and the hook shaped distal end extending transversely across at least a portion of the channel when the clip element is in the closed position.

16. An external retaining device according to claim 14 wherein the two side walls of the tube guide portion define a hollow space there between.

17. A method of retaining a catheter assembly to a patient, the method comprising the steps of:
placing a catheter having an elongate tube percutaneously in a patient;
providing an external retaining device including
a base member having a lower surface and an upper surface, the base member defining a passage therethrough from the lower surface to the upper surface, the passage having a central axis and configured for the elongate tube to be directed therethrough, the base member including a tube guide portion extending from the upper surface, the tube guide portion having two side walls extending upwardly from the base member and an elongate channel with a longitudinal axis defined therein, the channel being located between the side walls proximate an upper edge area of each side wall, at least one side wall being elastic for flexure toward the other side wall, and
a manually-operable clip assembly located proximate the channel of the tube guide portion, the clip assembly including at least one clip element mounted for pivotal movement selectively between a closed position and an open position, the at least one clip element of the clip assembly being mounted proximate the upper edge area of the elastic side wall for pivotal movement from the closed position to the open position by flexure of the elastic side wall toward the other side wall, the clip assembly capable of receiving the elongate tube directed through the passage when the clip assembly is in the open position and securing placement of
the elongate tube relative to the base member when the clip assembly is in the closed position;
directing the elongate tube of the catheter through the passage of the base member of the external retaining device;
moving the clip assembly to the open position by applying pressure to the elastic side wall to move the clip element pivotally from the closed position to the open position by flexure of the elastic side wall toward the other side wall;
positioning the elongate tube of the catheter in the clip assembly; and closing the clip assembly by pivotal movement of the clip element to the closed position to secure placement of the elongate tube of the catheter relative to the base member of the external retaining device.

18. A method according to claim 17 wherein the channel of the external retaining device provided during the providing step has a first section located proximate the passage, the longitudinal axis at the first section of the channel aligned substantially with the central axis of the passage, and further wherein the channel has a second section spaced from the first section of the channel with the longitudinal axis at the second section of the channel angled relative to the central axis of the passage, the clip assembly being located proximate the second section of the channel.

19. A method according to claim 18 wherein the at least one clip element of the external retaining device provided during the providing step has a hook-shaped distal end extending transversely across at least a portion of the channel when in the closed position.

20. A method according to claim 19 wherein the two side walls are elastic for flexure toward each other, at least one clip element of the clip assembly being mounted at the upper edge area of each side wall to be moved pivotally from the closed position to the open position by flexure of the side wall, and further wherein each clip element includes a stem affixed to the upper edge area of the side wall with the hook shaped distal end extending transversely across at least a portion of the channel when the clip element is in the closed position; the moving step including squeezing the two side walls toward each other to move the clip elements pivotally from the closed position to the open position by flexure of the side walls.

21. A method according to claim 19 wherein the two side walls of the external retaining device provided during the providing step define a hollow space there between.

* * * * *

UNITED STATES PATENT AND TRADEMARK OFFICE
CERTIFICATE OF CORRECTION

PATENT NO.     : 6,231,547 B1
DATED          : May 15, 2001
INVENTOR(S)    : Derek O'Hara

It is certified that error appears in the above-identified patent and that said Letters Patent is hereby corrected as shown below:

<u>Column 5,</u>
Line 27, replace "900" with -- 90° --

Signed and Sealed this

Eighth Day of October, 2002

*Attest:*

*Attesting Officer*

JAMES E. ROGAN
*Director of the United States Patent and Trademark Office*